United States Patent
Shi et al.

(10) Patent No.: US 10,889,804 B2
(45) Date of Patent: Jan. 12, 2021

(54) PANCREATIC STROMAL PROGENITOR CELLS

(71) Applicant: Alfred E. Mann Institute for Biomedical Engineering at the University of Southern California, Los Angeles, CA (US)

(72) Inventors: Songtao Shi, Thousand Oaks, CA (US); Jin Liu, Philadelphia, PA (US)

(73) Assignee: ALFRED E. MANN INSTITUTE FOR BIOMEDICAL ENGINEERING AT THE UNIVERSITY OF SOUTHERN CALIFORNIA, Los Angeles, CA (US)

( * ) Notice: Subject to any disclaimer, the term of this patent is extended or adjusted under 35 U.S.C. 154(b) by 0 days.

(21) Appl. No.: 15/572,768

(22) PCT Filed: May 11, 2016

(86) PCT No.: PCT/US2016/031762
§ 371 (c)(1),
(2) Date: Nov. 8, 2017

(87) PCT Pub. No.: WO2016/183141
PCT Pub. Date: Nov. 17, 2016

(65) Prior Publication Data
US 2018/0142213 A1  May 24, 2018

Related U.S. Application Data

(60) Provisional application No. 62/159,671, filed on May 11, 2015.

(51) Int. Cl.
| | |
|---|---|
| C12N 5/071 | (2010.01) |
| A61K 35/39 | (2015.01) |
| A61P 5/48 | (2006.01) |
| A61K 38/00 | (2006.01) |
| C12Q 1/6881 | (2018.01) |

(52) U.S. Cl.
CPC ............ *C12N 5/0678* (2013.01); *A61K 35/39* (2013.01); *A61K 38/00* (2013.01); *A61P 5/48* (2018.01); *C12Q 1/6881* (2013.01); *C12N 2501/2306* (2013.01); *C12N 2506/02* (2013.01); *C12N 2506/45* (2013.01); *C12Q 2600/136* (2013.01); *C12Q 2600/158* (2013.01)

(58) Field of Classification Search
CPC . C12N 5/0678; C12N 2501/2306; A61P 5/48; A61K 35/39
See application file for complete search history.

(56) References Cited

U.S. PATENT DOCUMENTS

| | | |
|---|---|---|
| 6,703,017 B1 | 3/2004 | Peck et al. |
| 2002/1982816 | 12/2002 | Roberts et al. |
| 2013/0034526 A1 | 2/2013 | Itskovitz-Eldor et al. |
| 2013/0309769 A1 | 11/2013 | Benvenisty et al. |

FOREIGN PATENT DOCUMENTS

| | | |
|---|---|---|
| EP | 2 185 691 B1 | 3/2018 |
| WO | 2005/005608 A2 | 1/2005 |
| WO | 2006/094286 A2 | 9/2006 |
| WO | 2006094286 A2 | 9/2006 |

OTHER PUBLICATIONS

Shimada et al. J Immunol 2002; 168:861-868.*
Masamune et al. J Gastroenterol (2009) 44:249-260.*
Rahman et al. "CD13 promotes mesenchymal stem cell-mediated regeneration of ischemic muscle" Front Physiol. 2013; 4: 402.*
Mato et al. "Identification of a pancreatic stellate cell population with properties of progenitor cells: new role for stellate cells in the pancreas" Biochem. J. (2009) 421, 181-191.*
Kordes "Stellate cells are mesenchymal stem cells" European Journal of Medical Research 2014, 19 (Suppl 1):S6, From 1st International Conference of Collaborative Research Center 974: Liver Damage and Regeneration Düsseldorf, Germany. Nov. 15-16, 2013.*
Jaster et al. "Extracellular signal regulated kinases are key mediators of mitogenic signals in rat pancreatic stellate cells" Gut 2002; 51:579-584.*
Unsal "Comparison of Therapeutic Characteristics of Islet Cell Transplantation Simultaneous with Pancreatic Mesenchymal Stem Cell Transplantation in Rats with Type 1 Diabetes Mellitus" Stem Cell Rev and Rep (2015) 11:526-532.*
Grisendi et al. "Understanding tumor-stroma interplays for targeted therapies by armed mesenchymal stromal progenitors: the Mesenkillers," Am J Cancer Res, May 28, 2011 (May 28, 2011) vol. 1, pp. 787-805.
International Search Report PCT/US2016/031762 dated Oct. 17, 2016.
Klimczak et al., "Mesenchymal Stromal Cells and Tissue-Specific Progenitor Cells: Their Role in Tissue Homeostasis", Hindawi Publishing Corporation, Stem Cells International, vol. 2016, pp. 1-11.
Omary et al., "The pancreatic stellate cell: a star on the rise in pancreatic diseases", The Journal of Clinical Investigation, vol. 117, No. 1, pp. 50-59, Jan. 2007.

(Continued)

*Primary Examiner* — Blaine Lankford
(74) *Attorney, Agent, or Firm* — Knobbe, Martens, Olson & Bear, LLP

(57) ABSTRACT

This disclosure relates to pancreatic stromal progenitor cells. This disclosure also relates to isolation of pancreatic stromal progenitor cells. This disclosure further relates to a composition comprising pancreatic stromal progenitor cells and preparation of this composition. This disclosure also relates to a treatment comprising administering a composition comprising pancreatic stromal progenitor cells. This disclosure also relates to a treatment of diabetes mellitus comprising administering a composition comprising pancreatic stromal progenitor cells.

22 Claims, 7 Drawing Sheets

(56) References Cited

OTHER PUBLICATIONS

Hinz, et al. "Biological Perspectives, The MyofibroblastOne Function, Multiple Origins", The American Journal of Pathology, vol. 170, No. 6, pp. 1807-1816, Jun. 2007.

Supplementary European Search Report dated Oct. 8, 2018 in European Application No. 16793405.8 (12 pages).

Davani, et al., "Human Islet-Derived Precursor Cells are Mesenchymal Stromal Cells That Differentiate and Mature to Hormone-Expressing Cells In Vivo," Stem Cells, vol. 25, No. 12, pp. 3215-3222, Jan. 1, 2007.

Ersek, et al., "Persistent circulating human insulin in sheep transplanted in utero with human mesenchymal stem cells," Experimental Hematology, vol. 38, No. 4, pp. 311-320, Apr. 1, 2010.

Hu, et al., "Isolation and identification of mesenchymal stem cells from human fetal pancreas," Journal of Laboratory and Clinical Medicine, vol. 141, pp. 342-349, May 1, 2003.

Noguchi, et al., "Characterization of Human Pancreatic Progenitor Cells," Cell Transplantation, vol. 19, No. 6-7, pp. 879-886, Jun. 1, 2010.

Zhang, et al., "Evaluation of islets derived from human fetal pancreatic progenitor cells in diabetes treatment," Stem Cell Research & Therapy, vol. 4, No. 6, p. 141, Nov. 22, 2013.

Rezania, et al., "Maturation of Human Embryonic Stem Cell-Derived Pancreatic Progenitors Into Functional Islets Capable of Treating Pre-existing Diabetes in Mice," Diabetes, vol. 61, No. 8, Aug. 1, 2012.

Larijani, et al., "A Simple and Cost-effective Method for Isolation and Expansion of Human Fetal Pancreas Derived Mesenchymal Stem Cells," Archives of Iranian Medicine, vol. 18, No. 11, Nov. 2015.

* cited by examiner

PANCREATIC STROMAL PROGENITOR CELLS

CROSS REFERENCE TO RELATED APPLICATIONS

This application claims the benefit of PCT International Application no. PCT/US2016/031762, entitled "Pancreatic Stromal Progenitor Cells" filed May 11, 2016, which claims the benefit of U.S. provisional patent application No. 62/159,671, entitled "Pancreas Stromal Progenitors," filed May 11, 2015, the entire content of which are incorporated herein by reference.

BACKGROUND

Technical Field

This disclosure relates to pancreatic stromal progenitor cells. This disclosure also relates to isolation of pancreatic stromal progenitor cells. This disclosure further relates to a composition comprising pancreatic stromal progenitor cells and preparation of this composition. This disclosure also relates to a treatment comprising administering a composition comprising pancreatic stromal progenitor cells. This disclosure also relates to a treatment of diabetes mellitus comprising administering a composition comprising pancreatic stromal progenitor cells.

Description of Related Art

The pancreas contains two glands that are intimately mixed together into one organ. The bulk of the pancreas is composed of "exocrine" cells that produce enzymes to help with the digestion of food. These exocrine cells release their enzymes into a series of progressively larger tubes (called ducts) that eventually join together to form the main pancreatic duct. The main pancreatic duct runs the length of the pancreas and drains the fluid produced by the exocrine cells into the duodenum, the first part of the small bowel. The second functional component of the pancreas is the "endocrine" pancreas. The endocrine pancreas is composed of small islands of cells, called the islets of Langerhans. These endocrine cells don't release their secretions into the pancreatic ducts, instead they release hormones, such as insulin and glucagon, into the blood stream, and these hormones in turn help control blood sugar (glucose) levels.

SUMMARY

This disclosure relates to pancreatic stromal progenitor cells. This disclosure also relates to isolation of pancreatic stromal progenitor cells. This disclosure further relates to a composition comprising pancreatic stromal progenitor cells and preparation of this composition. This disclosure also relates to a treatment comprising administering a composition comprising pancreatic stromal progenitor cells. This disclosure also relates to a treatment of diabetes mellitus comprising administering a composition comprising pancreatic stromal progenitor cells.

This disclosure also relates to a product. This product may comprise isolated pancreatic stromal progenitor cells (PSPs). This product may comprise a formulation comprising PSPs. PSPs may be isolated from pancreas. Pancreas may be a pancreas of a human or a non-human animal.

PSPs may have the following features. PSPs may show high IL6 ($IL6^{high}$). PSPs may show a higher level of IL6 as compared to that of bone marrow mesenchymal stem cells (BMSC). PSPs may be positive to Sca1, CD105, Vimentin, CD44, CD29, or a combination thereof. PSPs may be negative to CD13, CD73, CD34, CD45, or a combination thereof. PSPs may have capability to differentiate to osteogenic cells, adipogenic cells, or a combination thereof. PSPs may have a very limited capacity to differentiate to adipocytes. This may indicate that PSPs may be a different type of cells as compared to mesenchymal stem cells.

In some aspects, PSPs that express high levels of IL6 ($IL6^{high}$) may express higher levels of IL6 compared to BMSCs under the same conditions. In other aspects, the high level of IL6 is in comparison to other cells under the same conditions. For example, PSPs that express high levels of IL6 may be obtained by isolating, from a population of cells (e.g., through sub-culturing or other suitable methods), those cells that express IL6 at the highest levels under the desired conditions. In some examples, the PSPs that express high levels of IL6 may comprise the 30%, 20%, 10% or 5% of cells that express IL6 at the highest level relative to other cells under the same conditions. In other examples, the PSPs that express high levels of IL6 may comprise the 30%, 20%, 10% or 5% of cells that express IL6 at the highest level relative to other cells under the same conditions. Yet, in other examples, the PSPs may express IL6 at a level at least 10%, 25%, 50%, 70%, or 90% more than BMSCs' IL6 expression level, when the PSPs and the BMSCs are isolated under same conditions.

Such features of PSPs may be used to aid in isolation of PSPs. Examples are as follows. PSPs may be isolated from other cells by identifying cells that show high IL6 ($IL6^{high}$) and isolating these cells. PSPs may be isolated from other cells by identifying cells that show high IL6 ($IL6^{high}$) as compared to bone marrow stem cells and isolating these cells. PSPs may be isolated from other cells by identifying cells that are positive to Sca1, CD105, Vimentin, CD44, CD29, or a combination thereof; and isolating such cells from other cells. PSPs may be isolated from other cells by identifying cells that are negative to CD13, CD73, CD34, CD45, or a combination thereof; and isolating such cells from other cells. PSPs may be isolated from other cells by determining whether these cells have capability to differentiate to osteogenic cells, adipogenic cells, or a combination thereof; and isolating such cells from other cells.

This disclosure also relates to method of a treatment of a mammal. A treatment of a mammal may comprise administering the mammal a composition comprising PSPs. This treatment may protect streptozotocin-induced beta cell from impairment. This treatment may enhance beta cell-mediated insulin production. This treatment may be used in regulating insulin production. This treatment may be used in repairing pancreas. This treatment may be used in the treatment of a disease that leads to a pancreatic disease. In some embodiments, the mammal may be a human.

This treatment may also be useful in treatment of a mammal that has a disease that affects how the mammal body uses blood sugar. An example of such disease may be diabetes mellitus. This diabetes may be any type of diabetes. For example, the diabetes may be chronic or non-chronic. Chronic diabetes conditions may include type 1 diabetes and type 2 diabetes. Other examples of this disease include potentially reversible diabetes (that may include prediabetes, when blood sugar levels are higher than normal, but not high enough to be classified as diabetes), and gestational diabetes, which occurs during pregnancy but may resolve after the baby is delivered.

This treatment may also be used in repairing pancreas, pancreatic tissue regeneration, improving islet transplantation efficiency, and/or for islet cell regeneration.

PSPs may form pancreatic tissue with regenerated islets of Langerhans. This feature may be used in isolation of PSPs. PSPs may form pancreatic tissue with regenerated islets of Langerhans, when they are implanted into kidney capsule. This feature may be used in isolation of PSPs.

This disclosure relates to a composition. The composition may comprise a pancreatic stromal progenitor cell (PSP). The composition may comprise an amount of the PSPs effective for treatment of a human that has a disease that affects how the human body uses blood sugar. The PSP may comprise a human PSP. The PSPs may comprise human PSPs, and wherein the human PSPs may be isolated from a pancreatic tissue of a human.

The PSPs may express high levels of IL6 ($IL6^{high}$). The PSPs may express high levels of IL6 ($IL6^{high}$) as compared to of the IL6 expression of bone marrow mesenchymal stem cells (BMSCs) of a human.

The PSPs may be isolated from other cells by identifying cells that express high levels of IL6 ($IL6^{high}$) and isolating such cells. The PSPs may be isolated from other cells by identifying cells that express high levels of IL6 ($IL6^{high}$) as compared to bone marrow mesenchymal stem cells (BMSCs) of a human, and isolating such cells. The PSPs may be positive for Sca1, CD105, Vimentin, CD44, CD29, or any combination thereof. The PSPs may express high levels of IL6 ($IL6^{high}$) and may be positive for Sca1, CD105, Vimentin, CD44, CD29, or any combination thereof. The PSPs may be isolated from other cells by identifying cells that are positive for Sca1, CD105, Vimentin, CD44, CD29, or any combination thereof; and isolating such cells from the other cells. The PSPs may be isolated from other cells by identifying cells that express high levels of IL6 ($IL6^{high}$) and are positive for Sca1, CD105, Vimentin, CD44, CD29, or any combination thereof; and isolating such cells from the other cells.

The PSPs may be negative for CD13, CD73, CD34, CD45, or any combination thereof. The PSPs may express high levels of IL6 ($IL6^{high}$) and are negative for CD13, CD73, CD34, CD45, or any combination thereof. The PSPs may express high levels of IL6 ($IL6^{high}$); and may be positive for Sca1, CD105, Vimentin, CD44, CD29, or any combination thereof; and may be negative for CD13, CD73, CD34, CD45, or any combination thereof. The PSPs may be isolated from other cells by identifying cells that are negative for CD13, CD73, CD34, CD45, or any combination thereof; and isolating such cells from the other cells. The PSPs are isolated from other cells by identifying cells that express high levels of IL6 ($IL6^{high}$); and are positive for Sca1, CD105, Vimentin, CD44, CD29, or any combination thereof; and are negative for CD13, CD73, CD34, CD45, or any combination thereof; and isolating such cells from the other cells.

The PSPs may have capability to differentiate to osteogenic cells, adipogenic cells, or a combination thereof. The PSPs may be isolated from other cells by identifying cells that have capability to differentiate to osteogenic cells, adipogenic cells or a combination thereof; and isolating such cells from other cells.

This disclosure also relates to a method of treatment of a human. The treatment method may comprise administering the human an effective amount of a composition comprising PSPs. The human may have a disease that affects how the human body uses blood sugar. The disease may be diabetes mellitus. The disease may be a chronic diabetes or non-chronic diabetes. The disease may be type 1 diabetes or type 2 diabetes. The disease may be potentially reversible diabetes or gestational diabetes. The human may have a disease that leads to a pancreatic disease. The treatment may protect streptozotocin-induced beta cell from impairment. The treatment may enhance beta cell-mediated insulin production. The e treatment may regulate insulin production. The treatment may repair pancreas. The treatment may aid pancreatic tissue regeneration. The treatment may improve islet transplantation efficiency, and/or regenerates islet cells.

Any combination of features disclosed above may be possible and are thereby within the scope of this disclosure. For example, any combination of above products (e.g. compositions) and methods (e.g. methods of treatment) is within the scope of this disclosure.

These, as well as other components, steps, features, objects, benefits, and advantages, will now become clear from a review of the following detailed description of illustrative embodiments, the accompanying drawings, and the claims.

BRIEF DESCRIPTION OF DRAWINGS

The drawings are of illustrative embodiments. They do not illustrate all embodiments. Other embodiments may be used in addition or instead. Details that may be apparent or unnecessary may be omitted to save space or for more effective illustration. Some embodiments may be practiced with additional components or steps and/or without all of the components or steps that are illustrated. When the same numeral appears in different drawings, it refers to the same or like components or steps.

DETAILED DESCRIPTION OF ILLUSTRATIVE EMBODIMENTS

Figure 1A:
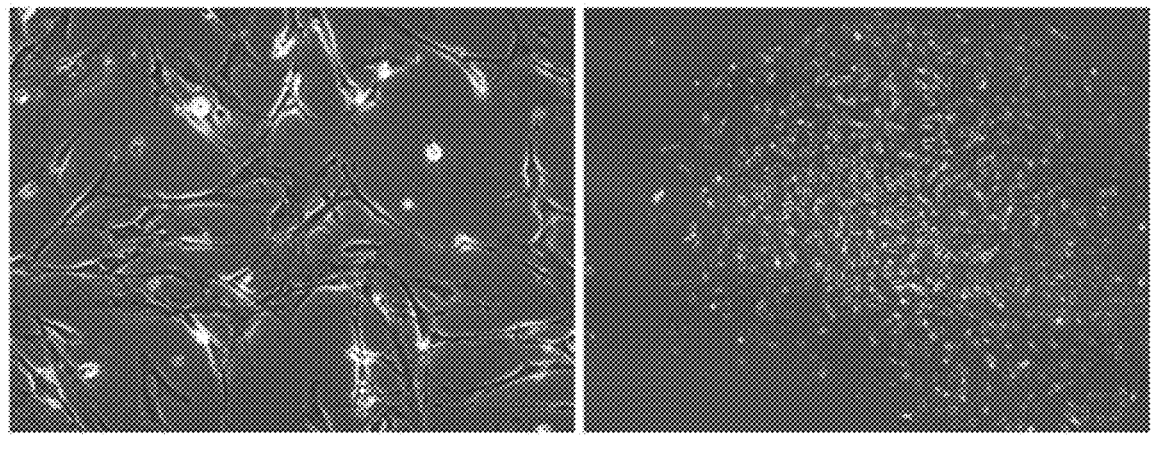
FIG. 1 (A) Microscopy images of isolated PSPs. (B) Colony clusters of PSPs at a low density and cultured for about 2 weeks.

Illustrative embodiments are now discussed. Other embodiments may be used in addition or instead. Certain details which may be apparent to a person of ordinary skill in the art or unnecessary may have been omitted from this disclosure to provide for a clear and concise disclosure. Conversely, some embodiments may be practiced without all of the details which are disclosed.

The following acronyms and abbreviations are used in this disclosure.

BMSCs: Bone marrow derived mesenchymal stem cells.
PSPs: Pancreatic stromal progenitors.
IL16: Interleukin 16.
MSC: Mesenchymal stem cell.
PBS: Phosphate-buffered saline.
DAPI: 4',6-diamidino-2-phenylindole This disclosure relates to pancreatic stromal progenitor cells. This disclosure also relates to isolation of pancreatic stromal progenitor cells. This disclosure further relates to a composition comprising pancreatic stromal progenitor cells and preparation of this composition. This disclosure also relates to a treatment comprising administering a composition comprising pancreatic stromal progenitor cells. This disclosure also relates to a treatment of diabetes mellitus comprising administering a composition comprising pancreatic stromal progenitor cells.

The treatments (methods) described herein can include, but are not limited to, diagnosis, therapy, cure, healing, mitigation, and/or prevention of a disease, and/or cosmetic treatment of a mammal. Exemplary methods for treatment (e.g., administering the compositions disclosed herein) include systemic injection or infusion, localized application or injection, or other suitable means of formulation and delivery.

The treatments described herein may be used to treat an animal, including but not limited to a mammal The mammal may be a human. The mammal may be a non-human animal. For example, the mammal may be a non-human primate, a horse, a sheep, cattle, a hog, a dog, a cat, or a goat.

This disclosure also relates to a composition. The composition may be a cell culture. The composition may be a drug or a biologic formulation.

Pancreatic stromal progenitor cells (PSPs), which are suitable for preparation of the exemplary composition, may be any progenitor cell of any mammal. For example, PSPs may be progenitor cells of a mammal that undergoes the treatment (i.e. autologous progenitor cell treatment). Or, the PSPs may be progenitor cells of a mammal other than the mammal that undergoes the treatment (i.e. allogeneic progenitor cell treatment). PSPs may be isolated from a pancreas of the mammal. PSPs may be isolated from a pancreas of a human.

This disclosure also relates to a method of treatment ("treatment method"). This treatment method may be useful in treatment of a human that has a disease that affects how the human body uses blood sugar. An example of such disease may be diabetes mellitus. This diabetes may be any type of diabetes. For example, the diabetes may be chronic or non-chronic. Chronic diabetes may include type 1 diabetes and type 2 diabetes. Other examples of this disease are potentially reversible diabetes (that may include prediabetes, when blood sugar levels are higher than normal, but not high enough to be classified as diabetes), and gestational diabetes, which occurs during pregnancy but may resolve after the baby is delivered.

This treatment may be used in the treatment of a disease that leads to a pancreatic disease. This treatment may protect streptozotocin-induced beta cell from impairment. This treatment may enhance beta cell-mediated insulin production. This treatment may be used in regulating insulin production. This treatment may be used in repairing pancreas. This treatment may also be used pancreatic tissue regeneration, improving islet transplantation efficiency, and/or for islet cell regeneration.

This disclosure also relates to a method of preparation of the composition ("preparation method"). One example of the preparation method may comprise obtaining a pancreatic tissue, separating the pancreatic tissue into cells, isolating PSPs (e.g., by sorting, selection for PSP markers or differentiation potential as described herein), and preparing a composition comprising the PSPs.

The pancreatic tissue may be any pancreatic tissue that contains a PSP. For example, the tissue may comprise a mammalian pancreatic tissue. The mammal may be a human. The mammal may also be a non-human animal. For example, the mammal may be a non-human primate, a horse, a sheep, cattle, a hog, a dog, a cat, and a goat.

Another example of the preparation method may comprise obtaining a plurality of pancreatic tissues, separating these tissues into cells, isolating PSPs (e.g., by sorting, selection for PSP markers or differentiation potential as described herein), and using the PSPs in the preparation of the composition. In this example, the plurality of pancreatic tissues may comprise tissues obtained from different tissues of a pancreas of a mammal.

The pancreatic tissue may be obtained from a mammal that undergoes the treatment. In this method, the treatment may be an autologous PSP cell treatment. The tissue may also be obtained from a mammal other than the mammal that undergoes the treatment. In this method, the treatment may be an allogeneic PSP cell treatment. Combination of said treatment methods may also be applied. For example, the treatment may comprise an autologous PSP cell treatment and an allogeneic PSP cell treatment.

Any suitable method may be used to separate the pancreatic tissue into cells, such as, a mechanical method, a chemical method, or a combination of a mechanical and a chemical method.

Examples of suitable mechanical methods include mincing, shredding, filtering, and the like. In other examples, the pancreatic tissue may be separated into cells by using homogenizers, ultrasonicators, ball mills, and the like. A combination of these mechanical methods may also be used to have separated cells.

Examples of suitable chemical method include digestion of the pancreatic tissue by using acids, bases, and enzymes. For example, a collagenase and a dispase may be used to digest the tissue. The collagenase may be collagenase type I. The dispase may be dispase II. For example, the pancreatic tissue may be digested by using phosphate buffered solution containing collagenase. A combination of these chemical methods may also be used to have separated cells.

The preparation method may further comprise preparing cell suspensions from the digested tissue by using a mechanical method. An example of such method may be filtering the digested tissue to obtain cell suspensions. The cell suspensions may be single-cell suspensions. For example, single-cell suspensions may be obtained by passing the digested pancreatic tissue through a 70-micrometer trainer.

Culturing the separated cells may comprise providing a solid surface, seeding the cells on the solid surface, culturing the seeded cells in a suitable culture media, and thereby obtaining a culture comprising cells that may be adherent to the solid surface ("adherent cells") and cells that may not be adherent to the solid surface ("non-adherent cells"). The adherent cells and/or non-adherent cells may be used in the preparation of the composition.

The solid surface may be a surface of any solid article suitable for culturing cells. For example, it may be a wall of a culture vessel. The culture vessel may be any desired culture vessel. For example, the culture vessel may be a petri dish or a cell-culture dish. The solid article may also be a bead or a particle. The solid article may have any desired size. For example, it may be a nano-particle.

The cell may be seeded using a solution. The solution may comprise a medium suitable for culturing the mammalian cell. An example of such medium may be a-MEM manufactured by Invitrogen (Carlsbad, Calif.). The solution may further comprise fetal bovine serum (FBS), L-glutamine, 2-mercaptoethanol, penicillin, and streptomycin.

The preparation method may further comprise eliminating from the culture the cells that are not adherent to the solid surface. For example, the culture may be washed using PBS or other suitable buffer to eliminate from the culture the cells that are not adherent to the solid surface.

The adherent cells may further be cultured, for example, in the same conditions disclosed above and/or used to prepare a cell composition in accordance with this disclosure.

The preparation method may further comprise dissociating from the solid surface the cells that may be adherent to the solid surface. The adherent cells may be dissociated from the solid surface by using an enzyme. The enzyme, for example, may be trypsin.

The preparation method may further comprise expanding the cultured cells. For example, the expanding the cultured cells may comprise doubling PSP cells by repetitively re-seeding (passaging) them using the preparation methods disclosed above.

The composition may comprise a pancreatic stromal progenitor cell (PSP). This composition may comprise an amount of PSPs effective in a treatment of a human that has a disease that affects how the human body uses blood sugar. The examples of such disease are disclosed above. The PSPs may comprise a human PSP.

The method of treating a human subject may comprise administering an effective amount of the composition comprising PSPs to the human subject, and thereby treating the disease that affects how the human body uses blood sugar. The composition may comprise an effective amount of the PSPs such that the composition is effective in treating the disease that affects how the human body uses blood sugar.

This disclosure also relates to a method of administration of the composition comprising a PSP ("administration method"). The administration method may comprise any method suitable for administration of a cell or a tissue. The administration method may comprise any method suitable for administration of PSPs. The composition comprising the PSPs suitable for the treatment purposes may be administered (or delivered) in various ways. For example, they may be infused, injected at various sites, or surgically implanted. In some embodiments, the method may comprise administration of a PSP, either as component of a single composition or as separate compositions. When administered as separate compositions, the compositions are administered to provide for overlap in the therapeutic activity of the PSPs.

The composition may be administered in an amount effective to treat a mammal. The amount of the PSPs in the composition ("dose") may be an amount effective to treat a mammal. The amount and/or concentration of PSPs in the composition can be selected to provide for convenient administration of an amount (of the composition that is acceptable for the mammal being treated). For example, a liquid composition that contains a high concentration of the PSPs is suitable for injection of a relatively small volume into solid tissue, while a liquid composition that contains a lower concentration of the PSPs may be advantageous for administration by intravenous infusion. Suitable liquid compositions may contain, for example, about $1\times10^1$ stem cells/mL to about $1\times10^{10}$ stem cells/mL, or about $1\times10^5$ stem cells/mL to about $1\times10^7$ stem cells/mL, or about $1\times10^6$ stem cells/mL to $5\times10^6$ stem cells/mL. Aggregated or solid compositions can contain, for example, about $1\times10^1$ stem cells/mg to about $1\times10^{10}$ stem cells/g.

The composition may comprise PSPs in an amount in the range of $1\times10^1$ stem cells/kg to $1\times10^{10}$ stem cells/kg, or $1\times10^5$ stem cells/kg to $1\times10^7$ stem cells/kg, or $1\times10^6$ stem cells/kg to $5\times10^6$ stem cells/kg.

The composition may also comprise PSPs in an amount in the range of $1\times10^1$ stem cells per kg of patient body to $1\times10^{10}$ stem cells/kg per kg of patient body; or $1\times10^5$ stem cells per kg of patient body to $1\times10^7$ stem cells per kg of patient body; or $1\times10^6$ stem cells per kg of patient body to $5\times10^6$ stem cells per kg of patient body.

For therapeutic purposes, an effective amount of the composition may be administered to a mammal in need thereof. An "effective amount" in an amount that produces the desired effect under the conditions of administration. For example, a therapeutically effective may be an amount sufficient to treat a diabetes mellitus. The exact dosage of PSPs to be administered may depend upon a variety of factors, including the age, weight, and sex of the mammal, the disease being treated, and the extent and severity thereof. A clinician of ordinary skill can determine the appropriate dose and method for administration based on these and other considerations.

Suitable compositions may include, for example, a PSP suspension in a liquid (preferably aqueous) medium, or the PSPs in aggregated form with or without solid supports or encapsulating materials. The liquid medium may be a pharmaceutically acceptable liquid medium. The liquid medium may also be suitable for injection. Some examples of suitable liquid media are generally well known, including but not limited to, normal saline (with or without glucose and/or potassium), Ringer's solution, Lactated Ringer's solution, and Hartmann's solution.

The composition may further comprise a carrier. The carrier may be suitable to host the PSPs. Example of the carrier may be in the form of matrices, tissues, fibers, beads, or other materials.

As will be understood by one of skill in the art, any combination of compositions comprising PSPs, methods of their preparation, and methods of their use or administration that are described herein may also be made and followed.

Other exemplary embodiments of this disclosure are as follows.

Example 1

Pancreatic Stromal Progenitors

We have developed methods to isolate IL6$^{high}$ pancreatic stromal progenitor cells (PSPs) from mouse pancreas and shown that PSPs express high levels of IL6 and are capable of forming colony clusters. In addition, PSPs are positive to Sca1, CD105, Vimentin, CD44, and CD29, but negative to CD13, CD73, CD34, and CD45. PSPs demonstrated the capability of differentiating to osteogenic cells and adipogenic cells. When cultured in vitro, PSPs demonstrated an ability to protect streptozotocin-induced beta cell from impairment and enhance beta cell-mediated insulin production. When implanted into kidney capsule, PSPs can form pancreatic tissue with regenerated islets of Langerhans.

Example 2

Isolation and Characterization of IL6$^{high}$ Pancreatic Stromal Progenitors

Mouse pancreatic tissues were minced into less than 1-3 mm$^2$ fragments and digested at about 37° C. for about 1 hour in sterile phosphate-buffered solution (PBS) containing about 1 mg/mL collagenase I (Worthington Biochemical Corporation, Lakewood, N.J.) and about 2 mg/ml dispase (Roche). The dissociated cell suspension was filtered through a 70 μm cell strainer (Falcon, Franklin Lakes, N.J.), and plated on non-treated 10-cm Petri dishes (VWR Scientific Products, Willard, Ohio) in minimum essential medium (MEM: Invitrogen) containing about 20% fetal bovine serum (FBS: Clontech Laboratories, Inc., Mountain View, Calif.), about 100 U/ml penicillin/streptomycin (Invitrogen), about 2 mM L-glutamine and about 550 μM 2-mercaptoethanol (2-ME; Sigma-Aldrich). The cells were continuously sub-cultured using about 0.05% trypsin containing about 1 mM EDTA and maintained in about 5% $CO_2$/95% air at about 37° C. in a humidified incubator (FIG. 1A).

Figure 1B:
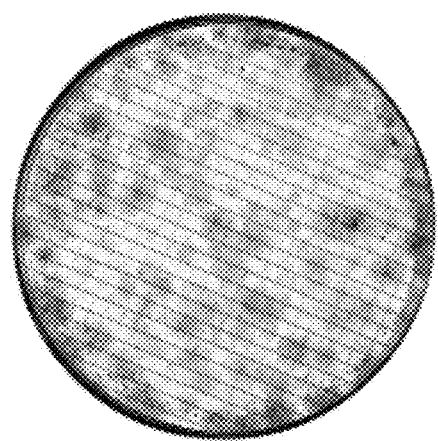

To assess colony-forming efficiency, day 10 cultures were fixed with about 4% paraformaldehyde, and then stained with about 0.1% toluidine blue. Aggregates of 50 cells were scored as colonies (FIG. 1B).

Figure 2A:
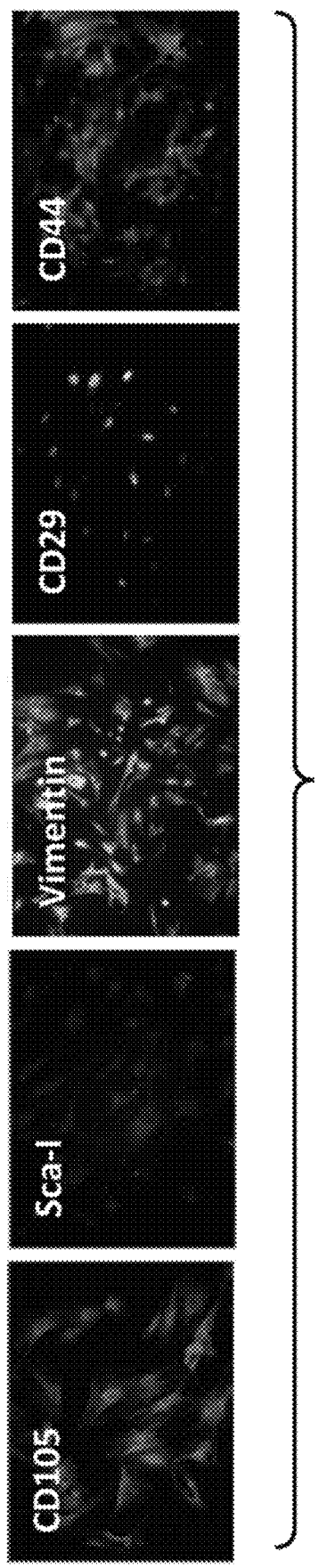
FIG. 2 (A) Immunofluorescence staining showed that PSPs expressed CD105, Sca1, vimentin, CD29, and CD44. (B) Flow Cytometric Analysis showed that PSPs were negative to CD13, CD34, CD45, and 73 antibody staining.

Immunofluorescence staining: about 4% paraformaldehyde-fixed cultured cells were immunolabeled with specific primary antibodies followed by Alexa Fluor® 488 and/or Alexa Fluor® 568-conjugated secondary antibodies (Molecular Probes, Inc. Life Technologies Corporation). The primary antibodies include CD105, Sca1, Vimentin, CD29, and CD44. After the nuclei were counterstained with 4',6-diamidino-2-phenylindole (DAPI), the samples were observed under a fluorescence microscope. Isotype-matched control antibodies (Invitrogen) were used as negative controls. These data showed that PSPs expressed CD105, Sca1, Vimentin, CD29, and CD44 (FIG. 2A).

Figure 2B:
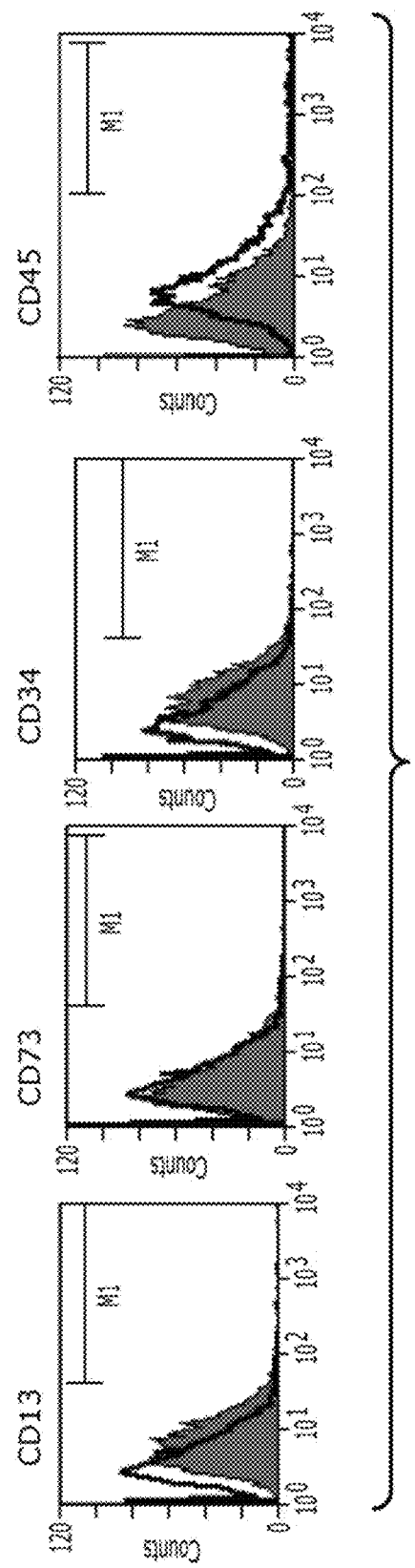

Flow Cytometric Analysis. Approximately 5×10$^5$ cells were incubated with specific PE- or FITC-conjugated mouse monoclonal antibodies for human CD13, CD34, CD45, and 73 or isotype-matched control IgGs (BD Biosciences) and subjected to flow cytometric analysis using a Beckman Coulter flow cytometer and FACScan program (BD Biosciences, San Jose, Calif.). Our data showed that PSPs were negative to CD13, CD34, CD45, and 73 antibody staining (FIG. 2B).

Figure 3A:
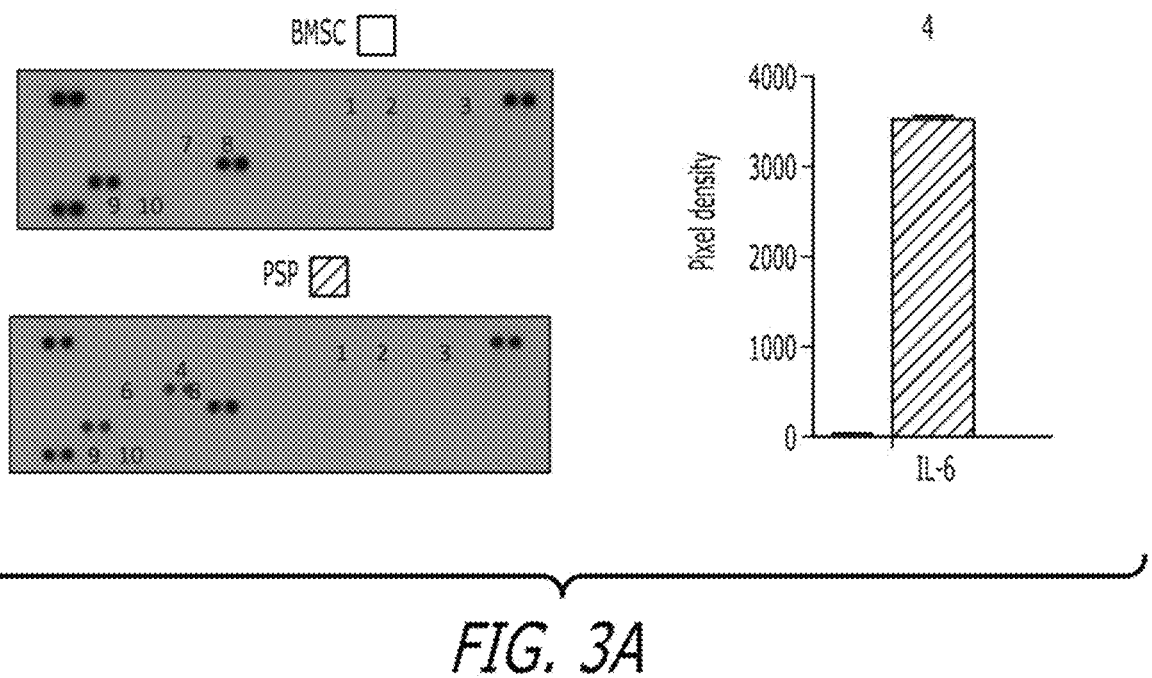
FIG. 3 (A) Cytokine array showed that PSPs expressed IL6, but bone marrow mesenchymal stem cells (BMSCs) failed to express IL6. (B) qPCR confirmed that PSPs expressed IL6, but BMSCs failed to express IL6. (C). Immunofluorescence staining showed that PSP expressed IL6, but BMSCs failed to express IL6.
Figure 3B:
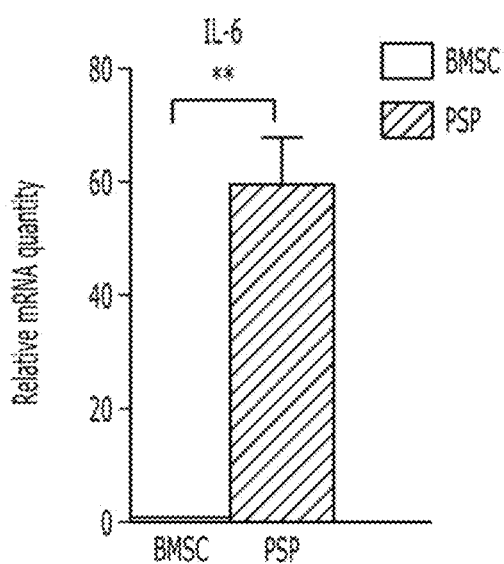
Figure 3C:
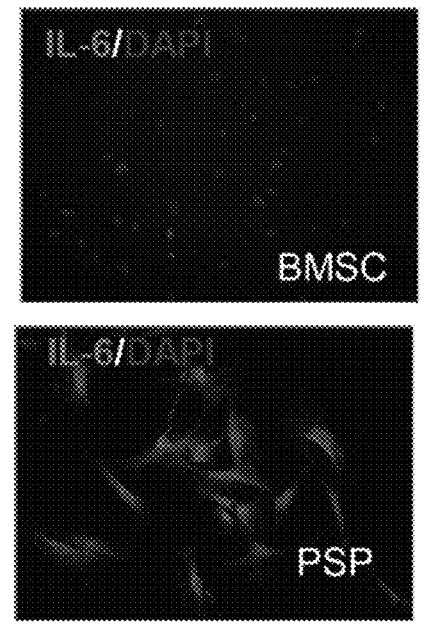

Cytokine array (R&D Systems, Inc.) analysis showed that PSP expressed elevated levels of IL6 when compared to bone marrow mesenchymal stem cells (FIG. 3A). After isolation of total RNA from cultured cells using an RNeasy Mini kit (Qiagen). qPCR and immunofluorescence staining confirmed that PSPs express higher levels of IL6 compared to BMSC (FIGS. 3B, 3C).

Figure 4A:
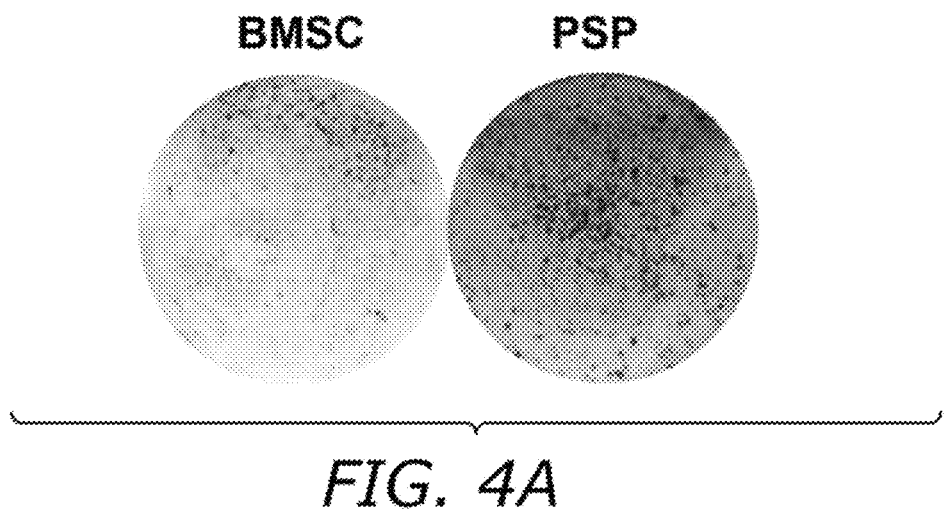
FIG. 4 (A) Alizarin red staining showed that PSPs had elevated in vitro osteogenic differentiation capacity compared to bone marrow mesenchymal stem cells (BMSC). (B) Oil red O staining showed that PSPs showed very limited capacity to differentiation to adipocytes compared to BMSCs.

PSPs were plated at 5×10$^5$ cells/well in 6-well plate in the culture medium, allowed to adhere overnight, and replaced with osteogenic Induction Medium (PT-3002, Cambrex, Charles City, Iowa) supplemented with dexamethasone, L-glutamine, ascorbic acid, and β-glycerophosphate. After 4-5 weeks, the in vitro mineralization was assayed by Alizarin red S (Sigma-Aldrich) staining. Our data showed that PSPs possess osteogenic differentiation capacity (FIG. 4A).

Figure 4B:
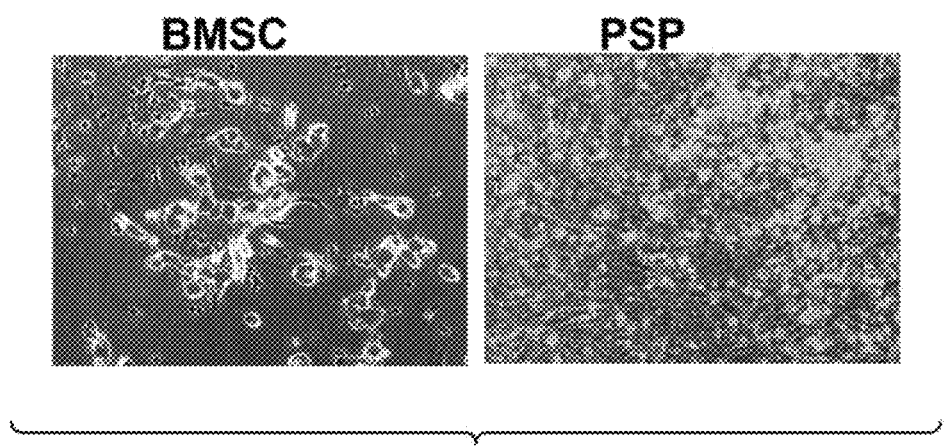

PSPs were plated in adipogenic induction medium supplemented with about 10 μM human insulin, about 1 μM dexamethasone, about 200 μM indomethacin, and about 0.5 mM 3-isobutyl-1-methylxanthine (Sigma-Aldrich, St Louis, Mo.). Oil Red O staining was performed to detect intracellular lipid vacuoles characteristic of adipocytes. Our data showed that PSPs had very limited capacity to differentiate to adipocyte (FIG. 4B).

Figure 5:
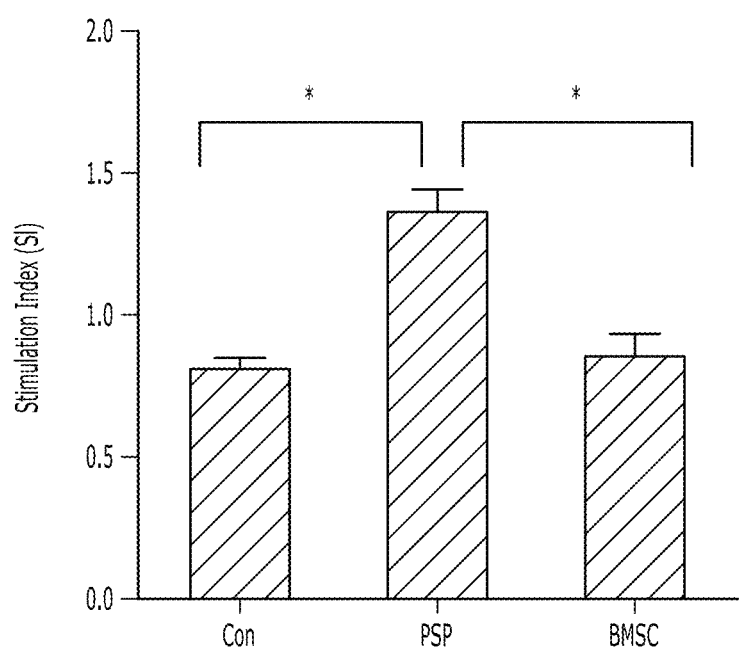
FIG. 5 Glucose-stimulated insulin secretion (GSIS) showed that PSPs can stimulate MIN6 beta cells produced more insulin when compared to BMSCs and un-stimulated control group.

Glucose-stimulated insulin secretion (GSIS). PSPs, cultured overnight at about 3.3 mM or about 11.1 mM glucose, MIN-6 cells were incubated with about 3.3 mM or about 16.7 mM glucose for about 1 h. Medium samples were collected and the levels of insulin and glycerol were measured. (FIG. 5).

Example 3

Kidney Capsule Implant

Figure 6A:
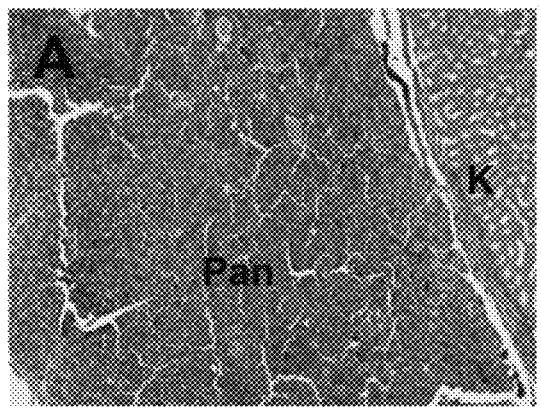
FIG. 6 (A) H&E staining showed that kidney capsule (K) implanted PSPc regenerated pancreas like tissue (Pan). (B) H&E staining showed that kidney capsule implanted PSPc regenerated pancreas like tissue (Pan) and the islets of Langerhans (arrow). (C, D) Immunofluorescence staining showed that islet cells express insulin (C) and glucagon (D).
Figure 6B:
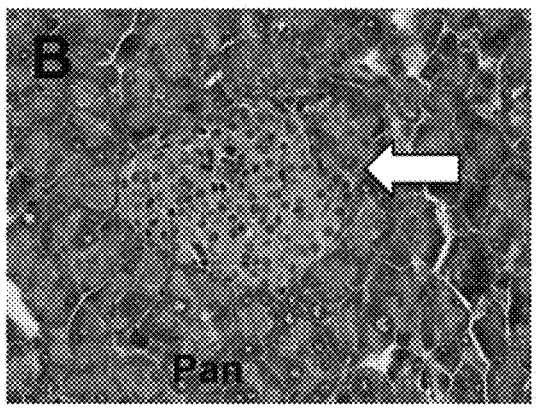
Figure 6C:
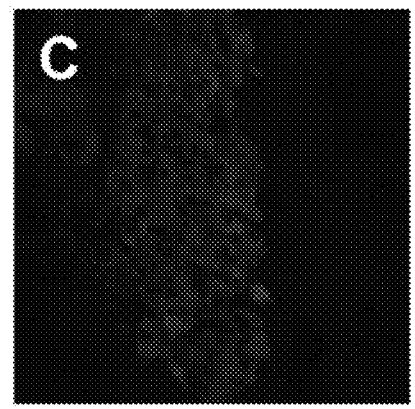
Figure 6D:
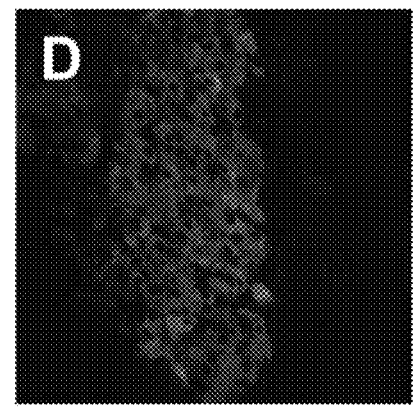

In order to determine the tissue regeneration and development, immunocompromised mice were anesthetized using Ketamine about 35 mg/kg BW IP, Xylazine about 5 mg/kg BW IP, and placed on its stomach on sterile surgical drapes. The skin in the surgical area on the back surface was shaved (nude mice was not shaved), which was followed by cleaning skin with 3 sets of alternating scrubs of betadine and alcohol. A small incision was made caudally along the spine. The skin was moved to the left and another incision was made with scissors right behind the rib cage over the kidney. The kidney capsule was opened with the fine tip of no. 5 forceps, and cell or tissue pellets were placed under the kidney capsule. Peritoneal cavity was sutured using 5/0 absorbable sutures. The skin incision was closed with 4-0 nylon and Dermabond. The animal was placed on a heating pad in a new cage with a watch card. When animals begin to recover from anesthesia, they were given buprenorphine (0.05-0.1 mg/kg subcutaneously) and observed closely for about 48 hours post-surgery. The mice were observed as described above and euthanized at 28-48 days after the operation for harvesting of the kidney capsule grafting products. H&E staining showed that implanted PSPs generated pancreatic cells and the islets of Langerhans structure (FIGS. 6A, 6B). Immunofluorescence staining showed that islet cells expressed insulin and glucagon (FIGS. 6C, 6D).

Any combination of products such as compositions comprising pancreatic stromal progenitors, methods of their preparation, and methods of their use that are described herein may also be made and followed.

The components, steps, features, objects, benefits, and advantages that have been discussed are merely illustrative. None of them, nor the discussions relating to them, are intended to limit the scope of protection in any way. Numerous other embodiments are also contemplated. These include embodiments that have fewer, additional, and/or different components, steps, features, objects, benefits, and/or advantages. These also include embodiments in which the components and/or steps are arranged and/or ordered differently.

Unless otherwise stated, all measurements, values, ratings, positions, magnitudes, sizes, and other specifications that are set forth in this disclosure are approximate, not exact. They are intended to have a reasonable range that is consistent with the functions to which they relate and with what is customary in the art to which they pertain.

All articles, patents, patent applications, and other publications that have been cited in this disclosure are incorporated herein by reference.

In this disclosure, the indefinite article "a" and phrases "one or more" and "at least one" are synonymous and mean "at least one".

Relational terms such as "first" and "second" and the like may be used solely to distinguish one entity or action from another, without necessarily requiring or implying any actual relationship or order between them. The terms "comprises," "comprising," and any other variation thereof when used in connection with a list of elements in the specification or claims are intended to indicate that the list is not exclusive and that other elements may be included. Similarly, an element preceded by an "a" or an "an" does not, without further constraints, preclude the existence of additional elements of the identical type.

The abstract is provided to help the reader quickly ascertain the nature of the technical disclosure. It is submitted with the understanding that it will not be used to interpret or limit the scope or meaning of the claims. In addition, various features in the foregoing detailed description are grouped together in various embodiments to streamline the disclosure. This method of disclosure should not be interpreted as requiring claimed embodiments to require more features than are expressly recited in each claim. Rather, as the following claims reflect, inventive subject matter lies in less than all features of a single disclosed embodiment. Thus, the following claims are hereby incorporated into the detailed description, with each claim standing on its own as separately claimed subject matter.

The invention claimed is:

1. A composition comprising:
human pancreatic stromal progenitor (PSP) cell suspension comprising from about $1\times10^1$ PSP cells/mL to about $1\times10^{10}$ PSP cells/mL, and a carrier, wherein the amount of PSP cells in the composition is effective for treatment of a human that has a disease that affects how the human body uses blood sugar;
wherein,
the human PSP cells consist of a subpopulation of PSP cells that are separated from an initial population of human PSP cells isolated from a pancreatic tissue of a human;
wherein the human PSP cells in the human PSP cell suspension consist of only the top 30% of PSP cells from the initial population of the human PSP cells isolated from the pancreatic tissue of the human that express IL6 at the highest level relative to the initial population of the human PSP cells isolated from the pancreatic tissue of the human; and
the PSP cells are positive for Sca1, CD1 OS, Vimentin, CD44, and CD29.

2. The composition of claim 1, wherein at least some of the PSP cells in the human PCP cell suspension are negative for CD13, CD73, CD34, CD45, or any combination thereof.

3. The composition of claim 1, wherein the PSPs have capability to differentiate to osteogenic cells, adipogenic cells, or a combination thereof.

4. The composition of claim 1, wherein the PSPs consist essentially of cells that have capability to differentiate to osteogenic cells, adipogenic cells or a combination thereof.

5. A method of treatment of a human comprising administering the human an effective amount of the composition of claim 1.

6. The method of claim 5, wherein the disease is diabetes mellitus.

7. The method of claim 5, wherein the disease is a chronic diabetes or non-chronic diabetes.

8. The method of claim 5, wherein the disease is type 1 diabetes or type 2 diabetes.

9. The method of claim 5, wherein the disease is potentially reversible diabetes or gestational diabetes.

10. The method of claim 5, wherein the human has a disease that leads to a pancreatic disease.

11. The method of claim 5, wherein the treatment protects streptozotocin-induced beta cell from impairment.

12. The method of claim 5, wherein the treatment enhances beta cell-mediated insulin production.

13. The method of claim 5, wherein the treatment regulates insulin production.

14. The method of claim 5, wherein the treatment repairs pancreas.

15. The method of claim 5, wherein the treatment aids pancreatic tissue regeneration.

16. The composition of claim 1, wherein the suspension is a single cell suspension.

17. The composition of claim 1, wherein the carrier is a pharmaceutically acceptable liquid medium.

18. The composition of claim 1, wherein the carrier is a matrix.

19. The composition of claim 1, wherein the carrier is a fiber.

20. The composition of claim 1, wherein the carrier is a bead.

21. The composition of claim 1, which is formulated for systemic injection or infusion.

22. A composition comprising:
human pancreatic stromal progenitor (PSP) cell suspension comprising from about $1\times10^1$ PSPs/mL to about $1\times10^{10}$ PSPs/mL, and a carrier, wherein the amount of PSP cells in the composition is effective for treatment of a human that has a disease that affects how the human body uses blood sugar;
wherein,
the human PSP cells in the cell suspension consist of a subpopulation of PSP cells that are separated from an initial population of human PSP cells isolated from a pancreatic tissue of a human;
wherein the human PSP cells in the human PSP cell suspension express IL6 at a level that places them in the top 30% of PSP cells, based on high IL6 expression level, relative to human PSP cells isolated from human pancreatic tissue under the same conditions; and
the PSP cells are positive for Sca1, CD1 OS, Vimentin, CD44, and CD29.

* * * * *

UNITED STATES PATENT AND TRADEMARK OFFICE
CERTIFICATE OF CORRECTION

PATENT NO. : 10,889,804 B2
APPLICATION NO. : 15/572768
DATED : January 12, 2021
INVENTOR(S) : Songtao Shi Page 1 of 1

It is certified that error appears in the above-identified patent and that said Letters Patent is hereby corrected as shown below:

On the Title Page

On page 2, in Column 1, item (56), Other Publications, Line 1, delete "MyofibroblastOne" and insert --Myofibroblast One--.

In the Specification

In Column 5, Line 13, delete "4',6" and insert --4', 6--.

In Column 5, Line 13, delete "phenylindole" and insert --phenylindole.--.

In Column 9, Line 31, delete "50" and insert --≥50--.

In Column 9, Line 39, delete "4',6" and insert --4', 6--.

In the Claims

In Column 11, Line 52, Claim 1, delete "CD1 OS," and insert --CD105,--.

In Column 11, Line 55, Claim 2, delete "PCP" and insert --PSP--.

In Column 12, Line 41, Claim 22, delete "PSPs/mL" and insert --PSP cells/mL--.

In Column 12, Line 42, Claim 22, delete "PSPs/mL" and insert --PSP cells/mL--.

In Column 12, Line 57 (approx.), Claim 22, delete "CD1 OS," and insert --CD105,--.

Signed and Sealed this
Sixteenth Day of March, 2021

Drew Hirshfeld
*Performing the Functions and Duties of the*
*Under Secretary of Commerce for Intellectual Property and*
*Director of the United States Patent and Trademark Office*